United States Patent
Fujii

(10) Patent No.: US 7,700,367 B2
(45) Date of Patent: Apr. 20, 2010

(54) METHOD OF MAKING LAMINA SPECIMEN

(75) Inventor: Toshiaki Fujii, Chiba (JP)

(73) Assignee: SII NanoTechnology Inc. (JP)

( * ) Notice: Subject to any disclaimer, the term of this patent is extended or adjusted under 35 U.S.C. 154(b) by 1106 days.

(21) Appl. No.: 10/563,515

(22) PCT Filed: Jul. 5, 2004

(86) PCT No.: PCT/JP2004/009868

§ 371 (c)(1),
(2), (4) Date: Feb. 2, 2006

(87) PCT Pub. No.: WO2005/003735

PCT Pub. Date: Jan. 13, 2005

(65) Prior Publication Data

US 2006/0157341 A1    Jul. 20, 2006

(30) Foreign Application Priority Data

Jul. 8, 2003    (JP) .............................. 2003-193512

(51) Int. Cl.
*G01N 1/00*    (2006.01)
(52) U.S. Cl. ..................................... 436/174
(58) Field of Classification Search .................. 436/174
See application file for complete search history.

(56) References Cited

U.S. PATENT DOCUMENTS

| 5,525,806 A | 6/1996 | Iwasaki et al. |
|---|---|---|
| 5,574,280 A | 11/1996 | Fujii et al. |
| 5,656,811 A | 8/1997 | Itoh et al. ................... 250/309 |
| 5,986,264 A | 11/1999 | Grunewald |
| 6,417,512 B1 | 7/2002 | Suzuki |
| 6,781,125 B2 | 8/2004 | Tokuda et al. ............... 250/310 |
| 7,276,691 B2* | 10/2007 | Kodama et al. ............. 250/309 |
| 2002/0050565 A1 | 5/2002 | Tokuda et al. |

FOREIGN PATENT DOCUMENTS

| EP | 1 209 737 A2 | 5/2002 |
|---|---|---|
| JP | 04-149945 | * 5/1992 |
| JP | 2004087174 | * 3/2004 |

OTHER PUBLICATIONS

JP2004-087174. Machine Translation Date May 4, 2009.*
Barna, A;; Pecz, B.; Menyhard, M. "TEM sample preparation by ion milling/amphorization." Micron, 1999, vol. 30, pp. 267-276.*
Patent Abstracts of Japan, Publication No. 2001-345360, Publication Date Dec. 14, 2001.
Patent Abstracts of Japan, Publication No. 09-257670, Publication Date Oct. 3, 1997.
Patent Abstracts of Japan, Publication No. 08-327514, Publication Date Dec. 13, 1996.

* cited by examiner

*Primary Examiner*—Walter D Griffin
*Assistant Examiner*—Bobby Ramdhanie
(74) *Attorney, Agent, or Firm*—Adams & Wilks

(57) ABSTRACT

In a method of making a lamina specimen, first and second ion beams are simultaneously used to sputter etch first and second side walls of a lamina region at the same time under first and second ion beam conditions. A scanning ion microscope observation of the lamina region is made using the second ion beam while sputter etching of the first and second side walls is continued using the first ion beam until the thickness of the lamina has a predetermined value.

1 Claim, 3 Drawing Sheets

SURFACE

CROSS SECTION (a)
(b)
(c)
(d)

(a)

(b)

METHOD OF MAKING LAMINA SPECIMEN

TECHNICAL FIELD

The present invention relates to a method of making a lamina sample for making the lamina sample for observing by a transmission electron microscope, which forms a lamina in a sample surface of a semiconductor device or the like, and a composite charged particle beam apparatus.

BACKGROUND ART

In recent years, in various devices such as a semiconductor device and a display device, in order to realize an improvement in function, their structures have become smaller and complicated. Especially, an element or wiring forming each device becomes a laminated structure in which thin films of several-atom levels have been overlapped, and a demand for observing that structure is high. For this reason, one general technique is that the lamina is taken out by forming it by using a focused ion beam in a sample surface predetermined place, and it is observed by a high resolving power microscope such as transmission electron microscope.

Hitherto, there is known a method in which, by using a composite apparatus comprising a focused ion beam irradiation system and an electron beam irradiation system, the lamina sample is made by sputtering-etching-working a desired place of the sample surface by the focused ion beam, the lamina having been made is taken out, and the lamina sample having been taken out is observed by the transmission electron microscope (for example, refer to Patent Document 1).

[Patent Document 1] JP-A-4-76437 Gazette (2nd page)
[Patent Document 2] JP-A-4-62748 Gazette (2nd page)

With a development of a device manufacturing technique, the structure of an object to be observed becomes fine. In order to observe this fine structure, although the transmission electron microscope is utilized, in order to observe the fine structure by the high resolving power microscope, there is shown the fact that, when performing a lamina sample making for the observation, damage to the lamina sample when the sputtering etching working by the focused ion beam (FIB) has been performed is made minimum and, at the same time, a shape confirmation of the lamina sample is performed in a scanning electron microscope (SEM) observation by an electron beam irradiation scan.

As shown in the Patent Document 2, in order to uniformize a thickness of the lamina sample, it is known to work the sample while being slanted. However, in such a working method, a method of controlling the thickness of the lamina is not known.

The present invention solves the above issue, and its object is to make it possible to accurately control the thickness of the lamina and, at the same time, make the lamina sample in a short time.

SUMMARY OF THE INVENTION

In order to solve the above problem, in the invention of the present application, there has been adapted such that, in a method of Sputtering-etching-working the sample surface by using the focused ion beam, the lamina sample is made while measuring the thickness of the lamina to thereby confirm the thickness by scan-irradiating a 2nd focused ion beam from a direction parallel to a side wall of the lamina having been formed.

Additionally, there has been adapted such that the working is performed by combining plural focused ion beams, thereby shortening a time required for the working.

Further, by using a twin-beam apparatus (FIB+FIB) or a dual-beam apparatus (FIB+SEM), a tilt angle of a stage of the apparatus has been made a direction in which an angle that a sample stage face forms with a plane containing each beam lens-barrel is alterable. This fact is explained by using FIG. 4.

Normally, like FIG. 4(a), a sample stage 7 is constituted so as to slant in a plane direction containing each of beam lens-barrels 1, 3.

In contrast to this, in the present invention, there becomes a constitution in which it slants with respect to an axis different by at least 90 degrees as shown in FIG. 4(b). By this fact, it is possible to measure the thickness of the lamina sample at the same time as capable of working by correcting a slant angle of the side wall by a 1st charged particle beam, or immediately. Or, additionally, there is contained also the fact that it slants in both the above directions. That is, there becomes a dual-tilt constitution having two slant axes in the twin-beam apparatus or the dual-beam apparatus.

That is, in the invention of the present application, first of all, there is characterized in that—in a method of making a lamina sample by forming a lamina part by etching-working by scan-irradiating a focused ion beam to a sample surface, and taking out the lamina part—at the same time as making the lamina part by an etching working of a 1st focused ion beam or with an irradiation of the 1st focused ion beam being temporarily interrupted, by scan-irradiating a 2nd focused ion beam in a direction parallel to a side wall of the lamina part having been made, a surface portion of the lamina is microscope-observed to thereby measure a thickness of the lamina part, and the etching working is finished by confirming the fact that the thickness of the lamina part has become a predetermined thickness.

Secondly, there is characterized in that—in a method of making a lamina sample by forming a lamina part by etching-working by scan-irradiating a focused ion beam to a sample surface, and taking out the lamina part, comprising a 1st process of etching-working both sides of a region, which is to be made a lamina, under a 1st focused ion beam condition by using a 1st focused ion beam, a 2nd process of etching-working a side wall of the region, which is to be made the lamina, by using the 1st focused ion beam subsequently to the 1st process under a 2nd focused ion beam condition in which is an acceleration voltage is low and/or a beam current is low in comparison with the 1st focused ion beam condition, and a 3rd process of measuring a thickness of the region, which is to be made the lamina, by microscope-observing a surface portion of the region, which is to be made the lamina, by scan-irradiating a 2nd focused ion beam in a direction parallel to a side wall of the region, which is to be made the lamina—the thickness of the region, which is to be made the lamina, is formed into a predetermined thickness while simultaneously performing or alternately repeating the 2nd process and the 3rd process.

Thirdly, a method of making a lamina sample by the invention of the present application is characterized in that, after having been formed into a 1st desired thickness by applying the 2nd and 3rd processes to a 1st side wall of the region which is to be made the lamina, it is formed into the predetermined thickness by applying the 2nd and 3rd processes to a 2nd side wall of the region which is to be made the lamina.

Fourthly, there is characterized in that, when etching-working the side wall of the region, which is to be made the lamina, in the 2nd process, the sample is slanted such that the 1st focused ion beam is irradiated to the side wall so as to correct its slant, thereby scan-irradiating the focused ion beam.

Fifthly, there is characterized in that—in a method of making a lamina sample by forming a lamina part by etching-working by scan-irradiating a focused ion beam to a sample surface, and taking out the lamina part, comprising a 1st process of etching-working both sides of a region, which is to be made a lamina, under a 1st focused ion beam condition by using a 1st focused ion beam, a 2nd process of etching-working a side wall of the region, which is to be made the lamina, by scan-irradiating a 2nd focused ion beam from a direction parallel to the side wall of the region, which is to be made the lamina, and an angle different from the 1st focused ion beam, and a 3rd process of measuring a thickness of the region, which is to be made the lamina, by microscope-observing a surface portion of the region, which is to be made the lamina, by scan-irradiating under a 2nd focused ion beam condition, in which an acceleration voltage is low in comparison with the 1st focused ion beam condition, by using the 1st focused ion beam—the thickness of the region, which is to be made the lamina, is formed into a predetermined thickness while simultaneously performing or alternately repeating the 2nd process and the 3rd process.

Sixthly, there is characterized by comprising—in a method of making a lamina sample by forming a lamina part by etching-working by scan-irradiating a focused ion beam to a sample surface, and taking out the lamina part—a 1st process of sputtering-etching-working a 1st worked region for exposing a 1st side wall of a region, which is to be made a lamina, under a 1st focused ion beam condition of a 1st focused ion beam and, at the same time, sputtering-etching-working a 2nd worked region for exposing a 2nd side wall of the region, which is to be made the lamina, under a 1st focused ion beam condition of a 2nd focused ion beam, a 2nd process of sputtering-etching-working the 2nd worked region under the 1st focused ion beam condition of the 1st focused ion beam and, at the same time, sputtering-etching-working the 1st worked region under the 1st focused ion beam condition of a 2nd focused ion beam, a 3rd process of microscope-observing a surface portion of the lamina by scan-irradiating under a 3rd focused ion beam condition of the 2nd focused ion beam at the same time as sputtering-etching-working the 1st side wall by slanting the sample such that the 1st focused ion beam enters so as to correct, in the 1st side wall, its slant under a 2nd focused ion beam condition in which an acceleration voltage is low and/or a beam current is low than the 1st focused ion beam condition by using the 1st focused ion beam, or with an irradiation of the 1st focused ion beam being temporarily interrupted, and finishing the etching working by the 1st focused ion beam by confirming the fact that a thickness of the lamina has become a 1st predetermined thickness by measuring the thickness of the lamina, and a 4th process of microscope-observing the surface portion of the lamina by scan-irradiating under the 3rd focused ion beam condition of the 2nd focused ion beam at the same time as sputtering-etching-working the 2nd side wall by slanting the sample such that the 1st focused ion beam enters so as to correct, in the 2nd side wall, its slant under the 2nd focused ion beam condition of the 1st focused ion beam, or with the irradiation of the 1st focused ion beam being temporarily interrupted, and finishing the etching working by the 1st focused ion beam by confirming the fact that the thickness of the lamina has become a 2nd predetermined thickness thinner than the 1st predetermined thickness by measuring the thickness of the lamina.

Seventhly, there is characterized by having a finishing process of sputtering-etching by irradiating an inert ion beam to the side wall of the region which is to be made the lamina, and in that, after a sputtering etching working by the inert ion beam, a thickness of the region, which is to be made the lamina, is made so as to become a desired thickness.

Eighthly, in an composite focused ion beam apparatus in the invention of the present application, there is characterized in that—in a composite focused ion beam apparatus comprising a 1st focused ion beam lens-barrel scan-irradiating an ion beam, which has generated from an ion source, to a sample surface while being focused, a 2nd focused ion beam lens-barrel scan-irradiating the ion beam, which has generated from the ion source, to the sample surface while being focused, and a sample stage which mounts a sample, has plural drive shafts and moves the sample in a three-dimensional space—a 1st focused ion beam having been irradiated from the 1st focused ion beam lens-barrel and a 2nd focused ion beam having been irradiated from the 2nd focused ion beam lens-barrel are disposed so as to be irradiated at different angles to the same place of the sample surface having been mounted to the sample stage, and the sample stage slants, with at least a 2nd plane intersecting perpendicularly to a 1st plane formed by the 1st focused ion beam lens-barrel and the 2nd focused ion beam lens-barrel being made a reference, so as to be capable of altering an angle with respect to the 1st plane.

Ninthly, in an composite focused ion beam apparatus by the invention of the present application, there is characterized in that—in a composite focused ion beam apparatus comprising a 1st focused ion beam lens-barrel scan-irradiating an ion beam, which has generated from an ion source, to a sample surface while being focused, a 2nd focused ion beam lens-barrel scan-irradiating the ion beam, which has generated from the ion source, to the sample surface while being focused, an inert ion beam lens-barrel scan-irradiating an ion beam, which has generated from an inert ion source, to the sample surface while being focused, and a sample stage which mounts a sample, has plural drive shafts and moves the sample in a three-dimensional space—the 1st focused ion beam lens-barrel, the 2nd focused ion beam lens-barrel and the inert ion beam lens-barrel are disposed on the same plane, a 1st focused ion beam having been irradiated from the 1st focused ion beam lens-barrel, a 2nd focused ion beam having been irradiated from the 2nd focused ion beam lens-barrel and an inert ion beam having been irradiated from the inert ion beam lens-barrel are disposed so as to be irradiated at different angles to the same place of the surface of the sample having been mounted to the sample stage, and the sample stage slants, with at least a 2nd plane intersecting perpendicularly to a 1st plane formed by the 1st focused ion beam lens-barrel, the 2nd focused ion beam lens-barrel and the inert ion beam lens-barrel being made a reference, so as to be capable of altering an angle with respect to the 1st plane.

DETAILED DESCRIPTION OF THE INVENTION

Figure 1:
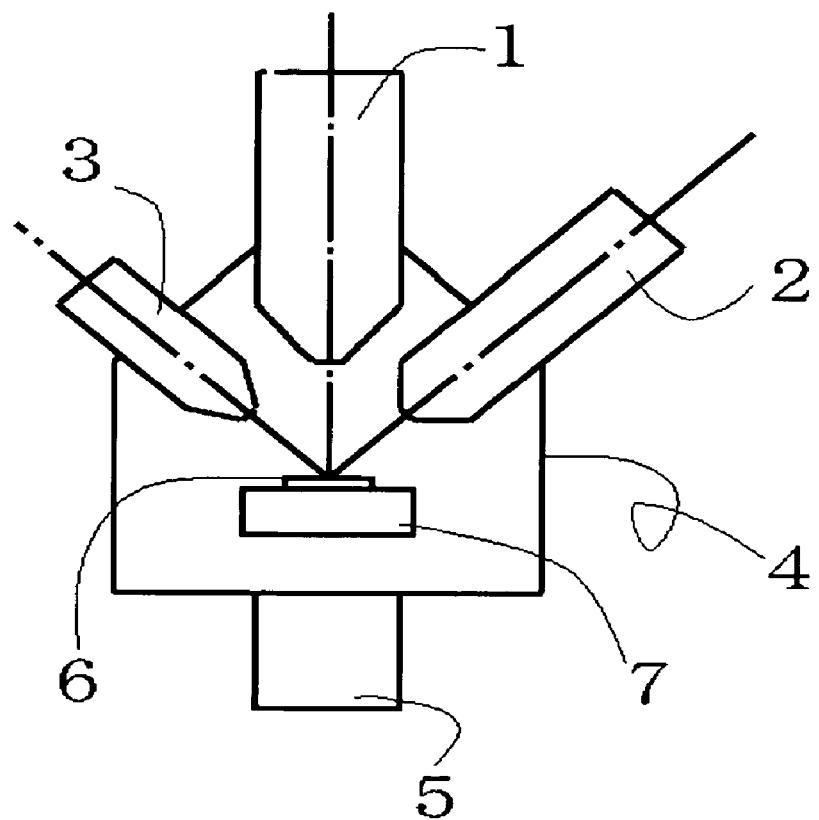
FIG. 1 is one constitution example of a focused ion beam composite apparatus according to the present invention.

One embodiment of an apparatus of the present invention is explained by being shown in FIG. 1.

To a sample chamber 4, there are attached a 1st focused ion beam lens-barrel 1 which focuses ions generating from a liquid metal ion source by a focused ion optical system and scan-irradiates them while being focused to a sample surface, a 2nd focused ion beam lens-barrel 2 which focuses the ions generating from the liquid metal ion source by the focused ion optical system and scan-irradiates them while being focused to the sample surface, and an inert ion beam lens-barrel 3 which generates an inert ion beam such as argon and irradiates it to a sample. An inside of the sample chamber is evacuated by a pump 5, thereby holding a high vacuum state. In an inner side of the sample chamber 4, there is installed a sample stage 7 mounting and moving a sample 6.

The 1st focused ion beam lens-barrel 1, the 2nd focused ion beam lens-barrel 2, and the inert ion beam lens-barrel 3 are disposed on the same plane. And, a 1st focused ion beam emitted from the 1st focused ion beam lens-barrel 1, a 2nd focused ion beam emitted from the 2nd focused ion beam lens-barrel 2, and an inert ion beam emitted from the inert ion beam lens-barrel 3 are adjusted so as to intersect in one place of a surface of the sample 6 having been mounted to the sample stage 7. At this time, dispositions of the 1st focused ion beam lens-barrel 1, the 2nd focused ion beam lens-barrel 2, and the inert ion beam lens-barrel 3 may be replaced.

Figure 2:
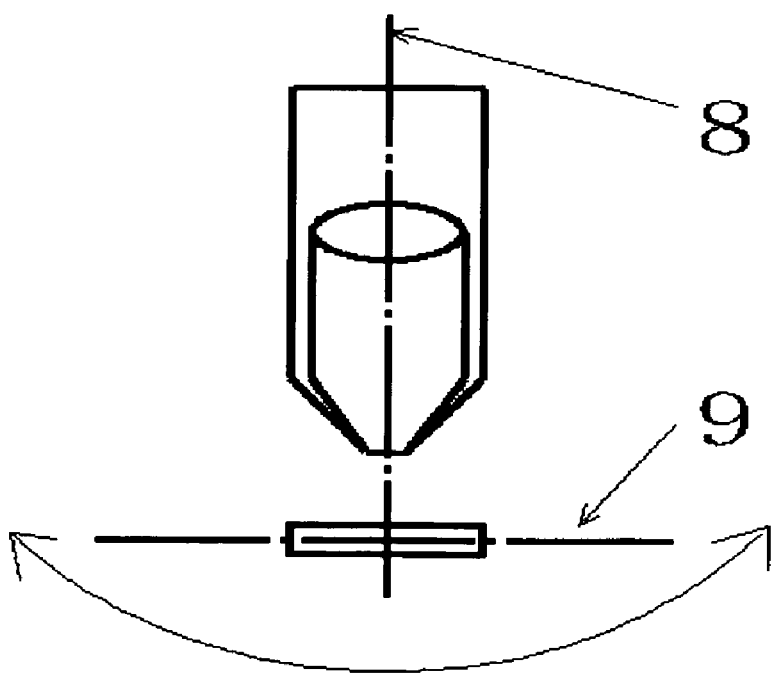
FIG. 2 is an explanatory view relating to an operation of a sample stage used in the focused ion beam composite apparatus of the present invention.

Although the sample stage 7 has plural drive shafts and is adapted so as to be capable of moving the sample in a three-dimensional space with the sample 6 mounted, it becomes a structure in which, as shown in FIG. 2, with a 2nd plane 9 intersecting perpendicularly to a 1st plane 8 containing the 1st focused ion beam lens-barrel 1, the 2nd focused ion beam lens-barrel 2 and the inert ion beam lens-barrel 3 being made a reference, their intersecting angles are alterable. It suffices if an alterable range of the intersecting angles is at least ±1 degree. This is a slant angle provided in order to stand up a side wall of the sample perpendicularly to the sample surface. If it can be experimentally slanted more than an angle of this degree, it is possible to correct a slant of a side wall face of the sample.

The 1st focused ion beam emitted from the 1st focused ion beam lens-barrel 1 and scan-irradiated to the sample surface sputtering-etching-works a worked region in the surface of the sample 6. At the same time or with the 1st focused ion beam being stopped, the 2nd focused ion beam emitted from the 2nd focused ion beam lens-barrel 2 and scan-irradiated to the sample surface is scan-irradiated to a region containing the worked region in the surface of the sample 6. And, secondary charged particles such as electrons generating from the sample 6 surface are detected by a secondary charged particle detector not shown in FIG. 1, and become a scanning electron microscope image by an apparatus control system similarly not shown in the drawing. Further, roles of the 1st focused ion beam lens-barrel 1 and the 2nd focused ion beam lens-barrel 2 can be replaces as well. Additionally, the 1st focused ion beam lens-barrel 1 and the 2nd focused ion beam lens-barrel 2 can similarly sputtering-etching-work the same place or different places of the sample surface as well.

In a case where a lamina sample is made by using the present apparatus, a state performing the sputtering etching work by one of the focused ion beams is observed by a scanning ion microscope image by a scan irradiation of the other of the focused ion beams and, when the thickness of the lamina has become a thickness having been set, the apparatus control system finishes the irradiations of the 1st and 2nd focused ion beams to the sample.

Further, after the lamina has been worked to a predetermined thickness by the focused ion beam, at the same time as performing the sputtering etching working by irradiating the inert ion beam, which is emitted from the inert ion beam lens-barrel 3, to a lamina periphery of the sample 6 surface, the lamina periphery is observed by the scanning ion microscope image by scan-irradiating any one of the 1st or 2nd focused ion beam and, when the thickness of the lamina has become the thickness having been set, the apparatus control system finishes the irradiations of the focused ion beam and the inert ion beam to the sample.

Figure 3:
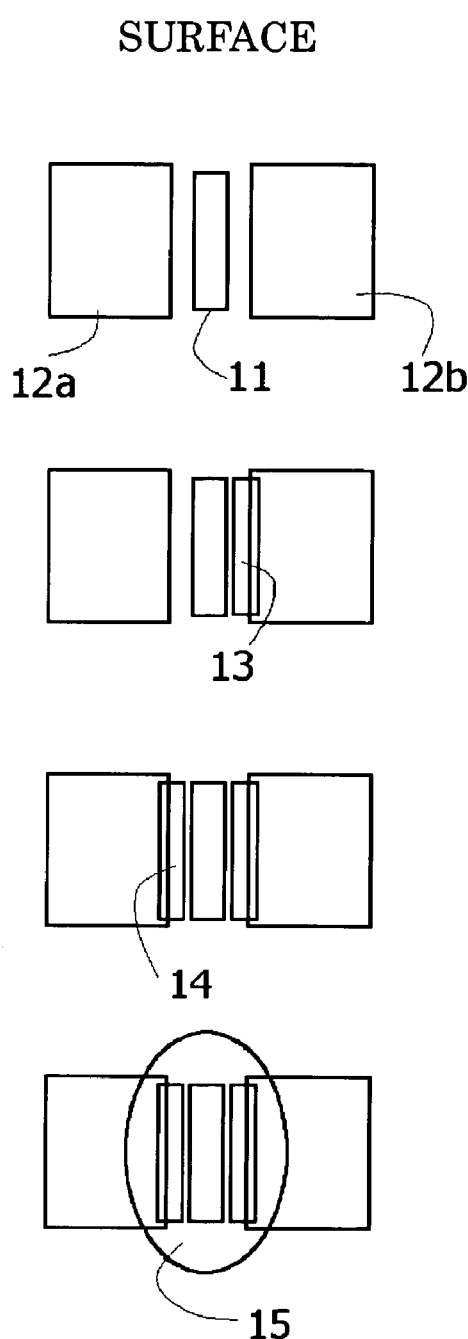
FIG. 3 is one embodiment of a method according to the present invention.
Figure 3:
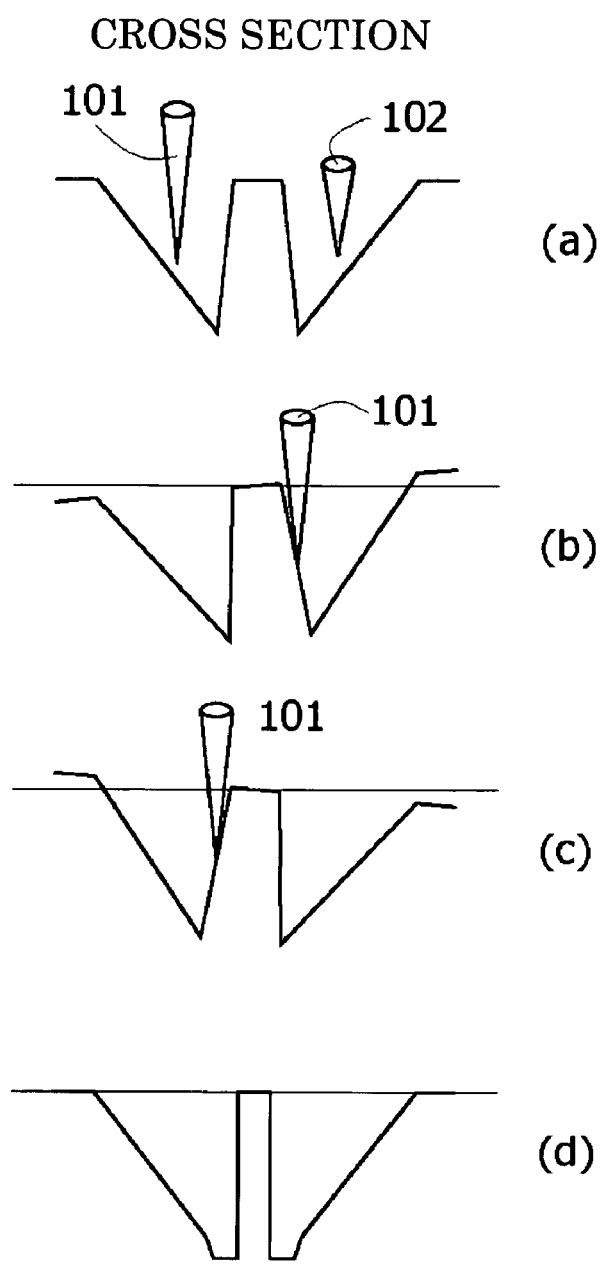
Figure 4:
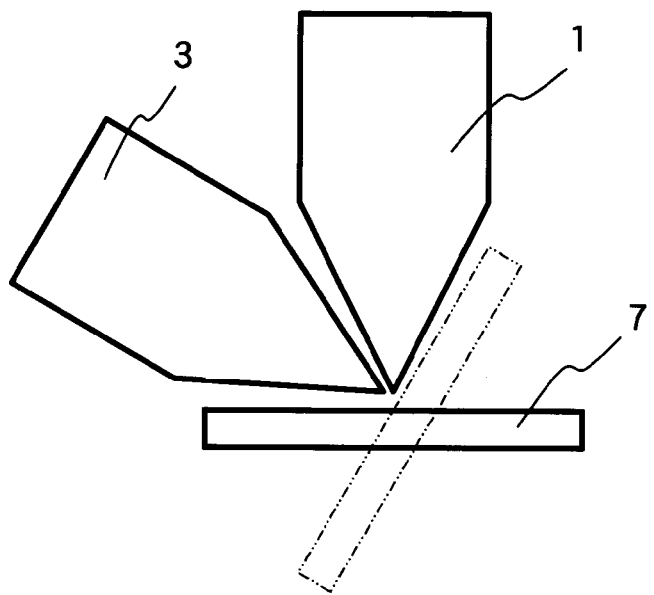
FIG. 4 is an explanatory view showing a tilt direction of the sample stage, wherein (a) is a front view, and (b) its side view.
Figure 4:
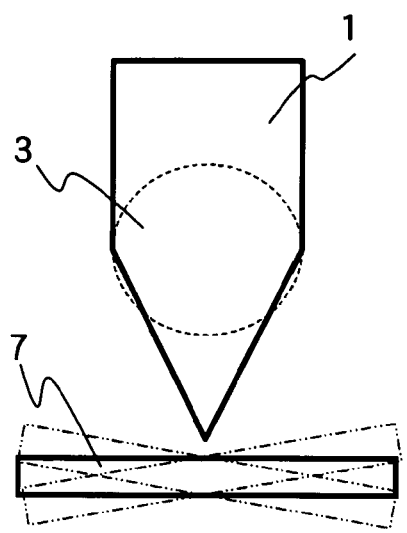

In FIG. 3, there is explained one embodiment of a method according to the present invention.

As shown in FIG. 3a, working frames 12a and 12b are set in both sides of a region 11, in the sample surface, to be left as the lamina.

And, at the same time as the working frame 12a is sputtering-etching-worked by a 1st focused ion beam 101, the working frame 12b is sputtering-etching-worked by a 2nd focused ion beam 102.

Subsequently, although not shown in the drawing, the working frame 12b is sputtering-etching-worked by the 1st focused ion beam, and the working frame 12a by the 2nd focused ion beam.

At this time, the 1st focused ion beam and the 2nd focused ion beam exist on a plane intersecting perpendicularly to the sample surface, and are disposed in a position where they enter at different angles into the same place of the sample surface. And, both of them perform the sputtering etching working under a 1st focused ion beam condition in which an acceleration voltage is high and an etching velocity is rapid.

As a result, both sides of a region having contained the region 11 to be left as the lamina are etching-worked.

Subsequently, as shown in FIG. 3b, a working frame 13 is set in one of side wall sides of the region 11 to be left as the lamina. And, the sample is slanted, and the sputtering etching working is performed by scan-irradiating the 1st focused ion beam 101 under a 2nd focused ion beam condition in which a beam diameter is small in comparison with the 1st focused ion beam condition. The slant angle is made one set such that aside wall of the lamina becomes perpendicular to the sample surface. At this time, while irradiating the 1st focused ion beam or with the 1st focused ion beam being stopped, a surface of the lamina is scanning-ion-microscope-observed by scan-irradiating the 2nd focused ion beam under a 3rd focused ion beam condition. And, when the thickness of the lamina has become a predetermined thickness, the irradiations of the 1st and 2nd focused ion beams are finished.

Subsequently, as shown in FIG. 3c, a working frame 14 is set in the other of side wall sides of the region 11 to be left as the lamina. And, the sample is slanted, and the sputtering etching working is performed by scan-irradiating the 1st focused ion beam 101 under the 2nd focused ion beam condition. The slant angle at this time is determined under the same condition as the other slant. Similarly to the process of FIG. 3b, the surface of the lamina is scanning-ion-microscope-observed by scan-irradiating the 2nd focused ion beam under the 3rd focused ion beam condition. And, when the thickness of the lamina has become the predetermined thickness, the irradiations of the 1st and 2nd focused ion beams are finished.

And, here, the lamina may be cut off from the sample by working surroundings of the lamina by the sputter etching working by the 1st or 2nd focused ion beam.

In a case where the injury due to the sputtering etching working by the focused ion beam, which is left in the lamina, influences on the observation by the transmission electron microscope, it may be performed by setting the acceleration voltage to a low voltage of 10 kV or lower under the 2nd focused ion beam condition.

Further, as shown in FIG. 3d, the sample is returned to a horizontality, and the inert ion beam is irradiated to a region 15 containing the lamina. And, the lamina periphery may be sputtering-etching-worked. At that time, the surface of the lamina is scanning-ion-microscope-observed by scan-irradiating the 1st or 2nd focused ion beam to the lamina periphery under the 3rd focused ion beam condition and, when the thickness of the lamina has become the predetermined thickness, the irradiations of the focused ion beam and the inert ion beam are finished.

Thereafter, similarly to the above, the lamina is cut off from the sample by working surroundings of the lamina by the sputtering etching working by the focused ion beam.

INDUSTRIAL APPLICABILITY

By the present invention, when forming the lamina in the sample surface, it is possible to accurately control the thickness of that lamina and, at the same time, to make the lamina sample in a short time. Further, although not explained by the embodiment and the like, from the fact that the thickness of the lamina is being observed by scan-irradiating the focused ion beam from a direction parallel to the side wall of the lamina, it is possible to obtain an advantage that it is possible to confirm also a uniformity of the thickness not only in an upper part of the lamina but also to a lower part of the same.

The invention claimed is:

1. A method of making a lamina sample by forming a lamina part by etching-working by scan-irradiating a focused ion beam to a sample surface, and taking out the lamina part, the method comprising:

a first process of sputtering-etching-working a 1st worked region for exposing a 1st side wall of a region, which is to be made a lamina, under a 1st focused ion beam condition of a 1st focused ion beam and, at the same time, sputtering-etching-working a 2nd worked region for exposing a 2nd side wall of the region, which is to be made the lamina, under a 1st focused ion beam condition of a 2nd focused ion beam, a second process of sputtering-etching-working the 2nd worked region under the 1st focused ion beam condition of the 1st focused ion beam and, at the same time, sputtering-etching-working the 1st worked region under a 1st focused ion beam condition of the 2nd focused ion beam, a third process of microscope-observing a surface portion of the lamina by scan-irradiating under a 3rd focused ion beam condition of the 2nd focused ion beam at the same time as sputtering-etching-working the 1st side wall by slanting the sample such that the 1st focused ion beam enters so as to correct, in the 1st side wall, its slant under a 2nd focused ion beam condition in which an acceleration voltage is low and/or a beam current is low relative to the 1st focused ion beam condition by using the 1st focused ion beam, or with an irradiation of the 1st focused ion beam being temporarily interrupted, and finishing the etching working by the 1st focused ion beam by confirming the fact that a thickness of the lamina has become a 1st predetermined thickness by measuring the thickness of the lamina, and a fourth process of microscope-observing the surface portion of the lamina by scan-irradiating under the 3rd focused ion beam condition of the 2nd focused ion beam at the same time as sputtering-etching-working the 2nd side wall by slanting the sample such that the 1st focused ion beam enters so as to correct, in the 2nd side wall, its slant under the 2nd focused ion beam condition of the 1st focused ion beam, or with the irradiation of the 1st focused ion beam being temporarily interrupted, and finishing the etching working by the 1st focused ion beam by confirming the fact that the thickness of the lamina has become a 2nd predetermined thickness thinner than the 1st predetermined thickness by measuring the thickness of the lamina.

* * * * *